United States Patent [19]

Cohen

[11] Patent Number: 4,752,646

[45] Date of Patent: Jun. 21, 1988

[54] 2-HALOCHROMANS

[75] Inventor: Noal Cohen, Montclair, N.J.

[73] Assignee: Hoffmann-La Roche Inc., Nutley, N.J.

[21] Appl. No.: 932,970

[22] Filed: Nov. 20, 1986

Related U.S. Application Data

[63] Continuation-in-part of Ser. No. 821,590, Jan. 23, 1986, abandoned.

[51] Int. Cl.$^4$ .............................................. C07D 311/72
[52] U.S. Cl. ..................................... 549/408; 549/410
[58] Field of Search ................................. 549/408, 410

[56] References Cited

U.S. PATENT DOCUMENTS 4,051,153  9/1977  Cohen .............................. 549/408

OTHER PUBLICATIONS

Bates, J. Org. Chem, 1983, 48 4479–4481.
Cohen, Helv. Chim Acta, vol. 61, Fasc 2 pp. 837–843 (1978).
Scott, Helv, Chim Acta, vol. 59, Fasc 1 pp. 290–306 (1976).
Foehlisch, Chem. Ber., 101, pp. 3990–4003 (1968).

*Primary Examiner*—Nicky Chan
*Attorney, Agent, or Firm*—Jon S. Saxe; George M. Gould; William H. Epstein

[57] ABSTRACT

Novel 2-halochromans and their coupling to various nucleophiles to produce Vitamin E and as well as novel intermediates for Vitamin E.

6 Claims, No Drawings

2-HALOCHROMANS

CROSS REFERENCE TO RELATED APPLICATIONS

This application is a continuation-in-part of U.S. application Ser. No. 06/821,590 filed Jan. 23, 1986, now abandoned.

SUMMARY OF THE INVENTION

In accordance with this invention, compounds of the formula:

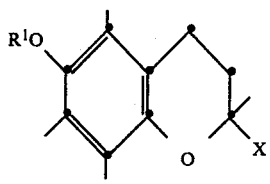

I to Vitamin E or intermediates thereof by reaction with a compound of the formula:

$$R^2Y \qquad \text{III}$$

wherein Y is an alkali metal or Mg X; $R^2$ is

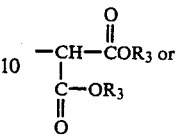

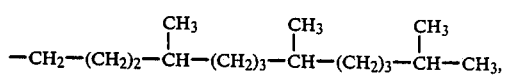

or $-CH_2-CH=CH_2$; $R^3$ is loweralkyl; and X is halogen.

In the reaction of the compound of formula I with the compound of formula III, depending upon $R^2$, the following compounds are formed

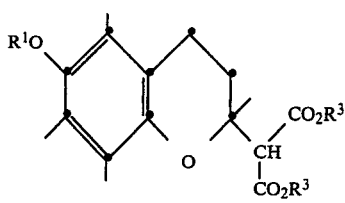

IV

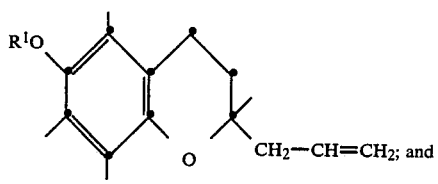

V

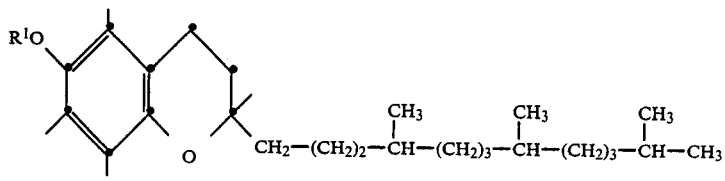

VI wherein X is halogen; and $R^1$ is methyl or a hydroxy protecting group removable by basic hydrolysis or hydrogenolysis;
are prepared from compounds of the formula:

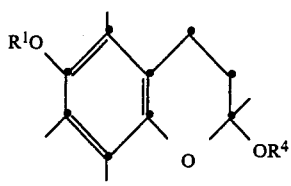

II wherein $R^1$ is as above, and $R^4$ is hydrogen or lower alkyl.

The compounds of formula I are intermediates in the formation of Vitamin E or other known intermediates thereof. The compounds of formula I can be converted wherein $R^1$ is as above; and $R^3$ is lower alkyl.

In accordance with this invention the compounds of formula IV and V are intermediates for Vitamin E, wherein the compound of formula VI is the immediate known precursor for Vitamin E.

DETAILED DESCRIPTION

As used throughout this application, the term halogen includes all four halogens i.e., fluorine, chlorine, bromine and iodine with chlorine, bromine and iodine being preferred and chlorine being especially preferred. Furthermore, as used throughout the application, the term "lower alkyl" includes both straight and branched chain alkyl groups having from 1 to 7 carbon atoms such as methyl, ethyl, propyl, n-butyl, isopropyl etc. with methyl and ethyl being preferred. Also as used herein, the term "lower alkanoic acids" comprehend an alkanoic acid of from 1 to 7 carbon atoms such as acetic acid, formic acid and propionic acid.

As also used herein, the term "aryl" signifies mononuclear aromatic hydrocarbon groups such as phenyl, which can be unsubstituted or substituted in one or more position with a lower alkylenedioxy, a halogen, nitro, lower alkyl or lower alkoxy substituent and polynuclear aryl groups such as naphthyl, which can be unsubstituted or substituted with one or more of the aforementioned groups. The preferred aryl group is the substituted or unsubstituted mononuclear aryl group, phenyl. The term "aryl lower alkyl" comprehends aryl lower alkyl groups wherein aryl and lower alkyl are as defined above, preferably those groups where lower alkyl is methyl. The preferred aryl lower alkyl substituent is benzyl. The term "aryl lower alkanoic acid" comprehends aryl lower alkanoic acid groups where "aryl" and "lower alkanoic acid" are as defined above and includes aryl carboxylic acids. The preferred "aryl lower alkanoic acid" being an arylcarboxylic acid such as benzoic acid.

As used herein, lower alkoxy comprehends lower alkoxy groups having 1 to 7 carbon atoms such as methoxy and ethoxy. The term "lower alkylenedioxy" designates lower alkylenedioxy group contain from 2 to 7 carbon atoms such as ethylenedioxy.

In the compound of formula II which is used as starting material for Vitamin E or intermediates for Vitamin E, $R^1$ can be any protecting group removable by basic hydrolysis or by hydrogenolysis. Therefore the conventional protecting groups removable either by basic hydrolysis or hydrogenolysis to yield the hydroxy group can be utilized as the protecting group $R^1$ in the process of this invention. Among these protecting groups are included ester groups derived from a lower alkanoic or aryl lower alkanoic acid. Any conventional method of forming these ester protecting groups can be utilized in the process of this invention. Any conventional ether protecting groups removable by hydrogenolysis can be utilized in this invention. Among the preferred ether protecting groups are the aryl methyl ethers such as benzyl ethers. These protecting groups can be removed by hydrogenolysis to yield the corresponding hydroxy group by conventional means well known in the art.

The compound of formula II is converted to the compound of formula I by treating the compound of formula II with a hydrohalic acid preferably hydrochloric acid at temperatures of from −30° C. to +30° C. preferably from −10° C. to +10° C. in a inert organic solvent medium. Generally, this reaction is carried out under anhydrous conditions. In carrying out this reaction, it is generally preferred to utilize an inert organic solvent. Any conventional ether solvent can be utilized to carry out this reaction. Among the preferred ether solvents are diethylether, tetrahydrofuran, glyme and diglyme.

In the next step of this invention, the compound of formula I is reacted with the compound of formula III to produce either the compound of formula IV or the compound of formula V or the compound of formula VI. Formation of either the compound of formula IV, V or VI will depend upon the precise substituent utilized for $R_2$ in the compound of formula III.

Where Y in the compound of formula III is an alkali metal, Y can be any conventional alkali metal, such as lithium, sodium or potassium with sodium and potassium being especially preferred. The reaction of the compound of formula I with the compound of formula III where Y is alkali metal is carried out under anhydrous conditions in an inert organic solvent medium. In carrying out this reaction any conventional inert organic solvent can be utilized as the reaction medium with ether solvents such as those mentioned hereinbefore being particularly suitable. The preferred inert organic solvent medium is diethylether. In carrying out this reaction temperature are from −30° C. to +30° C. can be utilized with temperatures of from 0° C. to 15° C. being especially preferred.

When Y in the compound of formula III is MgX, the compound of formula I and the compound of formula III are reacted to produce either the compound of formula IV, V or VI, depending upon $R^2$, in an inert organic solvent at temperatures ranging from −100° C. to 0° C. It is preferred to carry out this reaction at temperatures from −80° to −30° C. This reaction can be carried out at these temperatures in an inert organic solvent medium with the ethers such as those mentioned hereinbefore being especially suitable for this reaction.

In accordance with this invention the compounds of formula IV are converted to the known vitamin E intermediates of the formula:

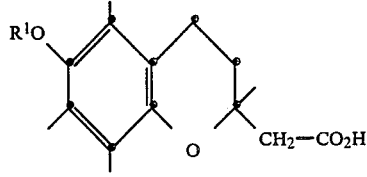

VII where $R^1$ is as above
by conventional procedures. Any conventional method for converting a malonic acid to an acetic acid can be utilized in this conversion. Among the preferred methods is hydrolysis followed by decarboxylation.

In accordance with this invention the compounds of formula V are converted to the known vitamin E intermediates of the formula:

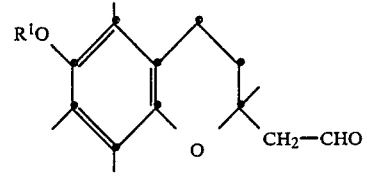

VIII wherein $R^1$ is as above;
by conventional procedures for converting a terminal double bond to an aldehyde among the preferred methods for carrying out this reaction is ozonolysis followed by a reductive workup.

In the Examples, reactions described below were carried out under an atmosphere of argon. Column chromatography was performed using EM Silica Gel 60 (0.063–0.2 mm). Anhydrous ether and tetrahydrofuran were distilled from sodium benzophenone ketyl immediately prior to use. The ether used in these Examples is diethyl ether.

EXAMPLE 1 rac-2-Chloro-3,4-dihydro-2,5,7,8-tetramethyl-6-(phenylmethoxy)-2H-1-benzopyran

To a solution of 5 g (16 mmol) of rac-3,4-dihydro-6-(phenylmethoxy)-2,5,7,8-tetramethyl-2H-1-benzopyran-2-ol in 50 mL of anhydrous ether was added 5 g of 4A molecular sieves. The mixture was stirred mechanically with ice-bath cooling while HCl gas was bubbled in for 30 min. Stirring was continued at 0° C. for 30 min and then the solvent was removed in vacuo. The residue was treated with 500 mL of hexane and the solution was decanted. The hexane solution was then treated with 10 g of anhydrous CaCl$_2$ and the mixture stirred for 2 hr. The solids were filtered and the filtrate was concentrated in vacuo to a volume of ca. 20 mL. Crystallization was induced by cooling to −10° C. and stirring, then the remaining solvent was removed in vacuo giving 4.9 g (92.8% yield) of rac-2-chloro-3,4-dihydro-2,5,7,8-tetramethyl-6-(phenylmethoxy)-2H-1-benzopyran as a colorless solid. The chlorochroman decomposed upon attempted column or thin layer chromatography. It was stored at 0° C.

EXAMPLE 2 rac-2-Chloro-3,4-dihydro-2,5,7,8-tetramethyl-2H-1-benzopyran-6-ol Acetate

A mixture of 10 g (37.9 mmol) of rac-3,4-dihydro-6-acetyloxy-2,5,7,8-tetramethyl-2H-1-benzopyran-2-ol and 10 g of 4A molecular sieves in 200 mL of anhydrous ether was stirred with ice-bath cooling while HCl gas was bubbled in for 30 min. The mixture was filtered and the filtrate concentrated in vacuo. The residue was taken up in 600 mL of hexane and anhydrous CaCl$_2$ was added. The mixture was stirred for 1 hr then filtered and the filtrate was concentrate in vacuo giving 4.3 g (40.2% yield) of rac-2-chloro-3,4-dihydro-2,5,7,8-tetramethyl-2H-1-benzopyran-6-ol acetate as a colorless solid, mp 102°–106° C., which was unstable to column or thin layer chromatography.

EXAMPLE 3 rac-3,4-Dihydro-2,5,7,8-tetramethyl-6-(phenylmethoxy)-2H-1-benzopyran-2-ylpropanedioic Acid Dimethyl Ester A 370 mg (9.25 mmol) sample of 60% by weight sodium hydride 40% by weight mineral oil dispersion was washed free of oil with hexane and treated with 20 mL of anhydrous tetrahydrofuran. The resulting slurry was stirred with ice-bath cooling while 1.056 g (8 mmol) of dimethyl malonate was added dropwise. After stirring for 10 min at 0° C., the sodiomalonate mixture was treated, dropwise, with a solution of rac-2-chloro-3,4-dihydro-2,5,7,8-tetramethyl-6-(phenylmethoxy)-2H-1-benzopyran in 4 mL of dry THF. Stirring at 0° C. was continued for 1.5 hr at which point the reaction mixture was poured into water and extracted three times with ether. The ether extracts were dried (MgSO$_4$), filtered, and concentrated in vacuo giving a yellow, oily residue. This material was dissolved in 5 mL of pet. ether (30° C.–60° C.) and stirred leading to a white precipitate. The solid was isolated by filtration and recrystallized from pet. ether giving 0.4 g (23.4% yield) of rac-3,4-dihydro-2,5,7,8-tetramethyl-6-(phenylmethoxy)-2H-1-benzopyran-2-ylpropanedioic acid dimethyl ester as a colorless solid, mp 80°–81° C.

EXAMPLE 4 rac-3,4-Dihydro-6-(phenylmethoxy)-2-(2-propenyl)-2,5,7,8-tetramethyl-2H-1-benzopyran To 12 mL (24 mmol) of 2M allylmagnesium chloride in tetrahydrofuran, cooled in an ice bath, was added, with stirring, a solution of 4.95 g (14.98 mmol) of rac-2-chloro-3,4-dihydro-2,5,7,8-tetramethyl-6-(phenylmethoxy)-2H-1-benzopyran in 60 mL of anhydrous ether. The reaction mixture was stirred at 0° C. for 6 hr then worked up by being poured into cold, saturated NH$_4$Cl solution and ether extraction. The product (5.4 g of a pale-yellow oil) was dissolved in 40 mL of methanol and 10 mL of ether containing 10 mg of p-toluenesulfonic acid monohydrate. The solution was stirred at room temperature for 21 hr then concentrated in vacuo. The residue was chromatographed on 75 g of silica gel. Elution with 40:1 parts by volume hexane-ether gave 2.88 g (57.2% yield) of rac-3,4-dihydro-6-(phenylmethoxy)-2-(2-propenyl)-2,5,7,8-tetramethyl-2H-1-benzopyran as a colorless oil.

EXAMPLE 5

(4R,8R)-1-Bromo-4,8,12-trimethyltridecane

A solution of 10.44 g (45.8 mmol) of (3R,7R)-3,7,11-trimethyldodecan-1-ol in 150 mL of anhydrous pyridine was stirred in an acetone-ice bath while 17.4 g (91.3 mmol) of p-toluenesulfonyl chloride was added in one portion. The mixture was stirred in the acetone-ice bath for 2 hr then kept at 0° C. for 40 hr before being quenched by the addition of 300 mL of ice-water. The product was isolated by extraction with 3×300 mL of ether. The ether extracts were combined, washed with 400 mL of cold 3N HCl and saturated brine, then dried (MgSO$_4$), filtered and concentrated in vacuo. There was obtained 16.6 g (94.9%) of (3R,7R)-3,7,11-trimethyldodecyl p-toluenesulfonate.

This tosylate (43.45 mmol) and 4.25 g (86.7 mmol) of sodium cyanide, in 80 mL of ethanol and 20 mL of water was stirred and refluxed for 2.5 hr. Most of the ethanol was removed in vacuo and the residue was treated with 75 mL of water and 75 mL of saturated brine and extracted with 3×100 mL of ether. The ether extracts were combined, washed with saturated brine, dried (MgSO$_4$), filtered through a plug of silica gel, and concentrated in vacuo. This afforded 10.25 g (99.5%) of (4R,8R)-4,8,12-trimethyltridecanenitrile as a yellow oil. GC analysis revealed a purity of 95.2%.

A mixture of this nitrile (43.25 mmol) and 18.4 g (0.33 mol) of potassium hydroxide in 162 mL of ethylene glycol and 13.5 mL of water was stirred in a 150° C. oil bath for 4 hr then cooled to 0°–5° C. and poured into 300 mL of 6N HCl. The mixture was extracted with 2×400 mL of ethyl acetate. The organic extracts were combined, washed with 300 mL of saturated brine, dried (MgSO$_4$), filtered and concentrated in vacuo giving 11.1 g (100%) of (4R,8R)-4,8,12-trimethyltridecanoic acid as an oil.

A solution of this acid in 50 mL of toluene was stirred at room temperature while 25 mL of sodium bis(2-methoxyethoxy)aluminum hydride in toluene was added dropwise. After being stirred for 3 hr at room temperature, the reaction mixture was decomposed by the cautious addition of 5 mL of ethanol. The mixture was then treated with 300 mL of 6N HCl and extracted with 3×300 mL of ethyl acetate. The organic extracts were combined, washed with 300 mL of saturated brine, dried (MgSO$_4$), filtered, and concentrated in vacuo. Kugelrohr distillation (160° C. bath temperature, 1 mm Hg) of the residue (9.7 g) gave 7.0 g of (4R,8R)-4,8,12-trimethyltridecanol as a colorless liquid having a GC purity of 94.5%. The distillation residue contained starting acid and was re-reduced with 6 mL of sodium bis(2-methoxyethoxy)aluminum hydride as described above. This provided an additional 1.8 g [total yield 8.8 g (84.2%)] of alcohol having a GC purity of 95.8%.

To a solution of 9.6 g (39.6 mmol) of (4R,8R)-4,8,12-trimethyltridecanol in 30 mL of anhydrous N,N-dimethylformamide was added 10.7 g (40.84 mmol) of triphenylphosphine. The solution was stirred in an acetone-ice bath (−10° C.) while 2.1 mL (41 mmol) of bromine was added dropwise. The temperature rose to 5° C. The reaction mixture was stirred at room temperature for 1 hr then poured into 100 mL of water and 150 mL of hexane. After filtration, the layers were separated and the aqueous phase was extracted with 2×150 mL of hexane. The hexane layers were washed with saturated NaHCO$_3$ solution, dried (MgSO$_4$), filtered through a plug of silica gel, and concentrated in vacuo. Kugelrohr distillation (150°–160° C. bath temperature, 1 mm Hg) of the residue gave 2 fractions: 5.15 g of 95.8% GC purity and 3.55 g of 97.9% GC purity (72.2% yield). Redistillation of the larger fraction gave (4R,8R)-1-bromo-4,8,12-trimethyltridecane as a colorless liquid bp 120° C. (0.15 mm) having a GC purity of 97.9%; $[a]^{25}D$-3.01° (c 2.09, hexane).

EXAMPLE 6

(2RS,4′R,8′R)-alpha-Tocopheryl Benzyl Ether

A Grignard solution was prepared from 0.28 g (11.2 mmol) of magnesium and 3.4 g (11.2 mmol) of (4R,8R)-1-bromo-4,8,12-trimethyltridecane in 25 mL of anhydrous ether. Grignard formation was induced with a few drops of 1,2-dibromoethane and the mixture was stirred and refluxed for 3.5 hr. To a stirred solution of 2.6 g (7.87 mmol) of rac-2-chloro-3,4-dihydro-2,5,7,8-tetramethyl-6-(phenylmethoxy)-2H-1-benzopyran in 25 mL of anhydrous ether, cooled to −10° C. (ice-acetone bath), was added the C$_{16}$-Grignard solution, dropwise. The resulting mixture was stirred at 0° C. for 18 hr then treated with 100 mL of saturated NH$_4$Cl solution. The product was isolated by extraction with 2×100 mL of ether. The ether extracts were washed with saturated brine, dried (MgSO$_4$), filtered, and concentrated in vacuo. The residue (4.95 g) was dissolved in 50 mL of methanol and 30 mL of ether containing 200 mg of p-toluenesulfonic acid monohydrate. After being stirred at room temperature for 24 hr, the solution was concentrated in vacuo and the residue was chromatographed on 200 g of silica gel. Elution with 40:1 parts by volume hexane-ether gave 1.82 g (44.5%) of pure (2RS,4′R,8′R)-alpha-tocopheryl benzyl ether. The identity of this material was proven by spectral and TLC comparison with an authentic sample of (2R,4′R,8′R)-alphatocopheryl benzyl ether.

EXAMPLE 7 rac-2-chloro-3,4-dihydro-2,5,7,8-tetramethyl-6-(phenylmethoxy)-2H-1-benzopyran

A mixture of 10 g of rac-2-methoxy-3,4-dihydro-2,5,7,8-tetramethyl-6-(phenylmethoxy)-2H-1-benzopyran, 10 g of calcium chloride, 100 ml of hexane and 50 ml of diethyl ether was stirred at −5° to −10° C. while HCl gas was bubbled in for 1 hr. An additional 10 g of calcium chloride was added and stirring was continued at room temperature for 2 hr. The mixture was filtered and the filtrate was concentrated in vacuo giving 10.2 g of title product as a light-brown oil. Proton NMR analysis revealed that this product consisted of 66% of the title compound and 33% of the starting 2-methoxy chroman.

EXAMPLE 8

A mixture of 0.43 g (1 mmole) of rac-3,4-dihydro-2,5,7,8-tetramethyl-6-(phenylmethoxy)-2H-1-benzopyran-2-ylpropanedioic acid dimethyl ester, 0.56 g (10 mmoles) of potassium hydroxide, and 25 ml of 9:1 ethylene glycol-water is stirred and refluxed for 8 hr. The mixture is cooled, diluted with water, and extracted with ether (the ether extract is discarded). The aqueous, alkaline solution is acidified with 3NHCl and the acid product isolated by ether extraction. The ether extracts are combined, washed with water and brine, dried (MgSO$_4$), filtered and concentrated in vacuo. Recrystallization of the residue from aqueous ethanol gives rac-3,4-dihydro-2,5,7,8-tetramethyl-6-(phenylmethoxy)-2H-1-benzopyran-2-acetic acid which can be converted to Vitamin E by the procedures in Helv. Chim Acta 61, 837 (1978); Helv. Chim. Acta 59, 290(1976) and Helv. Chim. Acta 64, 1158 (1981).

EXAMPLE 9

An ozone-oxygen gas mixture is passed into a solution of 0.67 g (2 mmoles) of rac-3,4-dihydro-2,5,7,8-tetramethyl-2-(2-propenyl)-6-(phenylmethoxy)-2H-1-benzopyran in 100 ml of methanol, with stirring, at −78° C. After the starting olefin has been consumed, the ozone flow is stopped and the solution is treated with excess dimethyl sulfide and allowed to warm to room temperature. The solution is concentrated in vacuo. The residue is chromatographed on silica gel giving rac-3,4-dihydro-2,5,7,8-tetramethyl-6-(phenylmethoxy)-2H-1-benzopyran-2-acetaldehyde, which can be converted to Vitamin E by the procedures in Helv. Chim. Acta set forth in Example 8.

EXAMPLE 10

A 0.6 g (2.13 mmole) sample of rac-2-chloro-3,4-dihydro-2,5,7,8-tetramethyl-2H-1-benzopyran-6-ol acetate is treated with (4R,8R)-4,8,12-trimethyltridecylmagnesium bromide as described in Example 6 except that an excess of the Grignard reagent is employed. Chromatography of the crude product on silica gel gives (2RS,4′R,8′R)-alpha-tocopherol as an oil.

EXAMPLE 11

Using the procedure of Example 6, rac-2-chloro-6-methoxy-3,4-dihydro-2,5,7,8-tetramethyl-2H-1-benzopyran is treated with (4R,8R)-4,8,12-trimethyltridecylmagnesium bromide to give (2RS,4′R,8′R)-alpha-tocopheryl methyl ether as an oil.

EXAMPLE 12

A solution of 0.25 g (0.56 mmole) of (2RS,4′R,8′R)-alpha-tocopheryl methyl ether in 10 ml of 1,2-dichloroethane is treated with 0.7 g (2.25 mmoles) of boron tribromide dimethyl sulfide complex and the reaction mixture is stirred and refluxed for 20 hr. The mixture is cooled and treated with water. The organic layer is separated, washed with water and brine, dried (MgSO$_4$), filtered and concentrated in vacuo. The residue is chromatographed on silica gel giving (2RS,4′R,8′R)-alpha-tocopherol as an oil.

EXAMPLE 13

A mixture of 84.3 g (0.337 mole) of rac.-2,6-dimethoxy-3,4-dihydro-2,5,7,8-tetramethyl-2H-1-benzopyran, 370 ml of acetone, 300 ml of water, and 2.5 ml of conc. hydrochloric acid was distilled until the distillate temperature reached 90° C. After being cooled, the mixture was diluted with water and extracted three times with ether. The ether extracts were combined, washed with saturated brine, dried (MgSO4), filtered, and concentrated in vacuo. The residue was recrystallized from aqueous acetone giving rac.-6-methoxy-3,4-dihydro-2,5,7,8-tetramethyl-2H-1-benzopyran-2-ol as an off-white solid, in crops of 34.6 g (43.5%) and 11.1 g (13.9%).

EXAMPLE 14

Using the procedure of Example 1, rac.-6-methoxy-3,4-dihydro-2,5,7,8-tetramethyl-2H-1-benzopyran-2-ol was converted into rac.-2-chloro-6-methoxy-3,4-dihydro-2,5,7,8-tetramethyl-2H-1-benzopyran, an off-white solid, in 90.2% yield.

EXAMPLE 15

Using the procedure of Example 3, except that diethyl malonate was employed in place of dimethyl malonate, rac.-2-chloro-6-methoxy-3,4-dihydro-2,5,7,8-tetramethyl-2H-1-benzopyran was converted into rac.-3,4-dihydro-2,5,7,8-tetramethyl-6-methoxy-2H-1-benzopyran-2-ylpropanedioic acid diethyl ester, a colorless solid, m.p. 74°-76° C., in 54% yield, purified by a combination of HPLC and recrystallization from pet. ether.

EXAMPLE 16

A mixture of 1.29 g (3.41 mmoles) of rac-3,4-dihydro-2,5,7,8-tetramethyl-6-methoxy-2H-1-benzopyran-2-ylpropanedioic acid diethyl ester, 1.68 g of potassium hydroxide, and 75 ml of 9:1 parts by volume ethylene glycol-water mixture was stirred and refluxed for 6 hours. The resulting mixture was poured on ice and extracted with ether (the ether extract was discarded). The aqueous solution was acidified with 3N HCl and the preciptated acid was extracted 3 times with ether. The combined ether extracts were washed with brine, dried (MgSO4), filtered and concentrated in vacuo. Purification of the residue by preparative thick layer chromatography gave 0.72 g (75.9%) of rac.-3,4-dihydro-6-methoxy-2,5,7,8-tetramethyl-2H-1-benzopyran-2-acetic acid, as a colorless solid, mp 96°-98° C. Demethylation using the procedure of example 14 gives rac.-3,4-dihydro-6-hydroxy-2,5,7,8-tetramethyl-2H-1-benzopyran-2-acetic acid which can be converted to alpha-tocopherol as described in Helv. Chim. Acta. 59, 290 (1976).

EXAMPLE 17

A mixture of 200 g (0.847 mole) of rac.-3,4-dihydro-2-methoxy-2,5,7,8-tetramethyl-2H-1-benzopyran-6-ol, 1200 ml of acetone, 200 ml of dimethyl sulfate, and 100 g of sodium hydroxide in 100 ml of water was stirred at room temperature for 4 hours whereupon 500 ml of 10% aqueous ammonium hydroxide solution was added and stirring continued for 30 minutes. The mixture was extracted 3 times with ether. The ether extracts were combined, washed with water and saturated brine, dried (MgSO4), filtered and concentrated in vacuo giving 238.4 g of residue which was recrystallized from ether-hexane at −20° C. There was obtained 145.9 g (68.9%) of rac.-2,6-dimethoxy-3,4-dihydro-2,5,7,8-tetramethyl-2H-1-benzopyran as a colorless solid. The product upon being recrystallized from hexane at −60° C., gave a solid, mp 37°-38° C.

Anal. Calcd. for $C_{15}H_{22}O_3$: C, 71.97; H, 8.86. Found: C, 71.84; H, 8.82.

I claim:

1. A compound of the formula

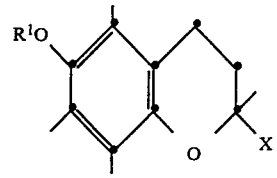

wherein X is halogen; and $R^1$ is methyl or a hydroxy protecting group removable by basic hydrolysis or hydrogenolysis.

2. The compound of claim 1 wherein X is chlorine.
3. The compound of claim 2 wherein $R^1$ is aralkyl.
4. The compound of claim 3 wherein said compound is 2-chloro-3,4-dihydro-2,5,7,8-tetramethyl-6-(phenylmethoxy)-2H-1-benzopyran.
5. The compound of claim 2 wherein $R^1$ is lower alkanoyl.
6. The compound of claim 5 wherein said compound is 2-chloro-3,4-dihydro 2,5,7,8-tetramethyl-2H-1-benzopyran-6-ol acetate.

* * * * *